United States Patent
Adolfsen

(12)
(10) Patent No.: US 6,623,971 B2
(45) Date of Patent: Sep. 23, 2003

(54) METHOD AND APPARATUS FOR CONDUCTING A STAT IMMUNOASSAY ANALYSIS IN A CAPSULE CHEMISTRY ANALYSIS SYSTEM

(75) Inventor: Robert Adolfsen, Montrose, NY (US)

(73) Assignee: Bayer Corporation

( * ) Notice: Subject to any disclaimer, the term of this patent is extended or adjusted under 35 U.S.C. 154(b) by 0 days.

(21) Appl. No.: 09/228,144

(22) Filed: Jan. 11, 1999

(65) Prior Publication Data

US 2003/0138357 A1 Jul. 24, 2003

(51) Int. Cl.[7] .................. G01N 35/08; G01N 35/00; G01N 1/10; G01N 21/76; G01N 15/06; G01N 21/00; G01N 31/00; G01N 21/64; G01N 21/29; G01N 21/41; G01N 33/00; G05B 1/00

(52) U.S. Cl. .................. 436/53; 436/43; 436/180; 436/172; 422/68.1; 422/82; 422/82.08; 422/82.05; 422/105

(58) Field of Search .................. 422/81, 82, 82.08, 422/82.05, 63, 105, 50, 61, 68.1, 69, 82.07, 82.09; 436/52, 43, 53, 172, 180

(56) References Cited

U.S. PATENT DOCUMENTS

| | | | | |
|---|---|---|---|---|
| 3,640,822 A | * | 2/1972 | Hrdina | 210/65 |
| 4,253,846 A | * | 3/1981 | Smythe et al. | 23/230 R |
| 5,268,147 A | | 12/1993 | Zabetakis et al. | 422/82 |
| 5,399,497 A | | 3/1995 | Kumar et al. | 436/53 |
| 5,466,946 A | | 11/1995 | Kleinschmitt et al. | 250/577 |
| 5,624,850 A | * | 4/1997 | Kumar | 436/527 |
| 5,631,167 A | * | 5/1997 | Adolfsen et al. | 436/53 |
| 5,714,388 A | * | 2/1998 | Kusnetz | 436/172 |
| 5,739,036 A | * | 4/1998 | Parris | 436/53 |
| 5,866,045 A | * | 2/1999 | Akhavan-Tafti et al. | 252/700 |
| 5,960,129 A | * | 9/1999 | Kleinschmitt | 385/12 |
| 6,120,734 A | * | 9/2000 | Lackie | 422/68.1 |
| 6,348,354 B1 | * | 2/2002 | Adolfsen et al. | |

* cited by examiner

*Primary Examiner*—Jill Warden
*Assistant Examiner*—Brian R Gordon
(74) *Attorney, Agent, or Firm*—Andrew L. Klawitter; John M. Paolino

(57) ABSTRACT

An apparatus and a method for analyzing a plurality of samples according to an analysis protocol is described, wherein each of the samples is contained within a liquid test package comprising a plurality of liquid and air segments including a reagent segment and wherein during at least a portion of the protocol the reagent segment emits photons. At least one of the liquid test pack includes a buffer segment separated from the reagent segment by a vanish bubble. The apparatus comprises a fluid conduit through which the liquid test packages are flowed, a first luminometer positioned along the fluid conduit for detecting photons emitted by the reagent segment of the at least one of the liquid test packages, a second luminometer positioned along the fluid conduit for detecting photons emitted by the reagent segments of the liquid test packages other than the at least one of the liquid test packages, and a vanish zone contained within the fluid conduit between the first and second luminometers. The reagent segment and the buffer segment of the at least one of the liquid test packages are mixed together in the vanish zone such that the light/photon producing reaction is substantially ceased. The method comprises the steps of inserting the liquid test packages into a fluid conduit, flowing the liquid test packages past a first luminometer positioned along the fluid conduit and detecting photons emitted by the reagent segment of the at least one of the liquid test packages, mixing the reagent segment and the buffer segment of the at least one of the liquid test packages after the photons have been detected, and flowing the liquid test packages past a second luminometer positioned along the fluid conduit and detecting photons emitted by the reagent segments of the liquid test packages other than the at least one of the liquid test packages.

4 Claims, 3 Drawing Sheets

METHOD AND APPARATUS FOR CONDUCTING A STAT IMMUNOASSAY ANALYSIS IN A CAPSULE CHEMISTRY ANALYSIS SYSTEM

FIELD OF THE INVENTION

The present invention relates to a capsule chemistry sample liquid analysis system adapted for the automated clinical analysis of pluralities of human biological sample liquids, in particular to a method and apparatus for conducting a stat immunoassay analysis in such a system.

BACKGROUND

U.S. Pat. Nos. 5,268,147 (the "'147 patent") and 5,399,497 (the "'497 patent"), owned by the assignee hereof, the disclosures of which are incorporated herein by reference, describe a capsule chemistry sample liquid analysis system which operates through repeated reversible, bi-directional flow of an appropriately configured stream of liquid test packages, each test package consisting of alternating segments of a liquid, such as a sample, reagent or buffer, and air, to enable repeated, precisely timed analysis of the sample of each of the test packages in the stream by one or more sample liquid analysis means. As described in the '147 and '497 patents, the system generally comprises a sample liquid test package metering and supply means which operates to meter successive test packages for reaction and analysis within the system; a reversible direction sample liquid test package displacement means which operates to bi-directionally displace the thusly metered and supplied test packages through the system; a test package transfer means which operates in conjunction with the test package metering and supply means and the test package displacement means to provide for the successive test package supply and bi-directional functions of the system; test package reaction and analysis means for analysis of the thusly supplied and displaced text packages; and detection means operatively associated with the reaction and analysis means to detect and quantify the successive sample liquid test package analysis results.

Such a system is particularly adapted to conduct automated clinical analysis of pluralities of human biological sample liquids and can be configured to perform various specific analyses, including a well known so called immunoassay analysis. An embodiment of the system just described configured for conducting an immunoassay analysis is shown in FIG. 1.

As described in detail in the '147 and '497 patents, the system generally operates by creating a plurality of test packages and successively inserting the test packages into analytical line 30 shown in FIG. 1, which preferably comprises a flexible conduit made of transparent Teflon or like material. Co-pending U.S. application Ser. No. 09/111,162, owned by the assignee hereof, the disclosure of which is incorporated herein by reference, describes in detail how the apparatus shown in FIG. 1, which includes an aspirating probe 10 connected to a service loop 15, a liquid supply 20, an aspiration pump 25, a transfer loop 35, and a shear valve 40, is able to create and subsequently insert the liquid test packages into the analytical line 30 for analysis. Accordingly, that discussion will not be repeated herein.

After insertion into the analytical line 30, the test packages are repeatedly and bi-directionally flowed back and forth in the analytical line 30, through operation of the stream pump 46 shown in FIG. 1, and ultimately past the appropriate test package reaction, analysis and detection means. Depending on the type of analysis being done, particular devices are disposed along the analytical line 30 so as to comprise the reaction, analysis and detection means. As shown in FIG. 1, a configuration appropriate for conducting an immunoassay analysis includes vanish zone 50, first, second and third bubble detectors 55, first and second magnets 60 and luminometer 65. The functionality of these components is described in greater detail both below and in the '147 and '497 patents.

It will be apparent to one of skill in the art that a test package suitable for a so-called sandwich type magnetic particle-based heterogeneous immunoassay is as shown in FIG. 2. In particular, this test package consists of six liquid segments: a magnetic particle suspension designated as MP, a mixture of sample and first and second reagents designated as $S/R_1/R_2$, a first wash designated as $W_1$, a second wash designated as $W_2$, a combination of a third reagent and a fourth reagent designated as $R_3/R_4$, and a marker dye designated as D. As illustrated in FIG. 2, each of these liquid segments is separated by an air segment It will also be apparent to one of skill in the art that additional suitable immunoassay protocols, and thus additional immunoassay test packages, exist, for example a test package containing eight liquid segments. In addition, the test package shown in FIG. 2, as well as the one described below and shown in FIG. 3, could include an additional buffer liquid segment as the first liquid segment.

As will be known by one of skill in the art, in a typical sandwich immunoassay analysis which utilizes the test package shown in FIG. 2, the sample S is allowed to react with first and second reagents $R_1$ and $R_2$ within the test package for a particular, fixed period of time as defined by the assay protocol. Then, the magnetic particles are transferred out of the magnetic particle suspension MP and into the $S/R_1/R_2$ segment, where they are allowed to mix for an additional specified amount of time as defined by the assay protocol. Thereafter, the magnetic particles are separated from the $S/R_1/R_2$ segment, are transferred to and washed in washes $W_1$ and $W_1$, and are transferred to and reacted with a combination of third and fourth reagents $R_3/R_4$. The reaction between the magnetic particles and the combination of third and fourth reagents $R_3/R_4$ generates a detectable response in the form of emitted photons which are in proportion to the analyte concentration in the sample S. The $R_3/R_4$ segment which is emitting photons is commonly referred to as a glowing segment. As noted above, a suitable apparatus for carrying out such an immunoassay is shown in FIG. 1 and includes first and second magnets 60, first, second and third bubble detectors 55 and luminometer 65. The first magnet 60 is used to transfer the magnetic particles into the $S/R_1/R_2$ segment after a specific amount of time, and the second magnet 60 is used to transfer the magnetic particles from the $S/R_1/R_2$ segment into washes $W_1$ and $W_2$ and ultimately into the $R_3/R_4$ segment. The luminometer 65 is used to detect and measure the photons emitted from the segment $R_3/R_4$ containing the magnetic particles. Bubble detectors 55 are capable of sensing an interface between an air segment and a liquid segment in a flowing stream of air and liquid segments and thus are used to track the flow of the stream of test packages in the analytical line 30. Bubble detectors are well known in the art, examples of which are described in U.S. Pat. No. 5,466,946 and U.S. application Ser. No. 08/995,738, both owned by the assignee hereof, the disclosures of which are incorporated herein by reference.

In the sandwich immunoassay analysis just described, the time that it takes for the reactions and various washes to be completed, and thus ultimately the time that it takes to yield a glowing segment that can be analyzed, is typically relatively long, for example, on the order of twenty minutes. It may, however, often be desirable to obtain analysis results for a particular sample S in a much shorter time period. A so-called stat immunoassay, which utilizes the test package shown in FIG. 3, has been developed for providing analysis results in a quicker fashion. As can be seen by comparing FIG. 2 and FIG. 3, the conventional immunoassay test package, i.e., a non-stat immunoassay test package, and the stat immunoassay test package differ in that for the stat immunoassay, the magnetic particular suspension MP is aspirated along with the sample S, the reagent $R_1$ and the reagent $R_2$ when the test package is created, rather than being separated therefrom by an air segment. Thus, for a stat immunoassay, the immunochemical reactions start as soon as the test package is created, and therefore a measurement can be made much sooner after the test package has been created.

As will be apparent to one of skill in the art, in order to use such a stat immunoassay package in a system such as the one shown in FIG. 1, it would be necessary to insert additional hardware along the analytical line 30, in particular at least an additional magnet and an additional luminometer at a position relatively close to the point where the test packages are inserted into the analytical line 30. Such a configuration and use of a stat immunoassay would, however, create a significant problem. In particular, as will be apparent to one of skill in the art, if a stat immunoassay test package as shown in FIG. 3 were to be inserted into the analytical line 30 along with other conventional immunoassay test packages, there would be, for a period of time during which the stat immunoassay test package is in the analytical line 30, two glowing segments in the analytical line 30 at the same time. The presence of two glowing segments in the analytical line 30 at the same time can result in photons from one glowing segment, i.e., the stat immunoassay glowing segment, being transmitted through the analytical line 30 and scattered into the detector of the luminometer 65 that is measuring the photons being emitted by the glowing segment of a conventional immunoassay test package. This phenomenon, known as optical carryover, will in most cases cause an error in the readings taken by that luminometer 65.

SUMMARY OF THE INVENTION

According to an aspect of the present invention, an apparatus for analyzing a plurality of samples according to an analysis protocol is provided, wherein each of the samples is contained within a liquid test package comprising a plurality of liquid and air segments including a reagent segment, and wherein during at least a portion of the protocol the reagent segment emits photons. At least one of the liquid test package includes a buffer segment separated from the reagent segment by a vanish bubble. The apparatus comprises a fluid conduit through which the liquid test packages are flowed, a first luminometer positioned along the fluid conduit for detecting photons emitted by the reagent segment of the at least one of the liquid test packages, a second luminometer positioned along the fluid conduit for detecting photons emitted by the reagent segments of the liquid test packages other than the at least one of the liquid test packages, and a vanish zone contained within the fluid conduit between the first and second luminometers. The reagent segment and the buffer segment of the at least one of the liquid test packages are mixed together in the vanish zone.

According to a further aspect of the present invention, the reagent segments emit photons as a result of a light-producing reaction requiring a high pH level, the buffer segments have a low pH level, and when the buffer segments and the reagent segments are mixed in the vanish zone, the light-producing reaction substantially ceases. According to still a further aspect of the present invention, each of the liquid test packages includes a segment containing magnetic particles. The apparatus according to this aspect further comprises a magnet positioned along the fluid conduit at a location in front of the first luminometer, the magnetic being adapted to transfer the magnetic particles of the at least one of the liquid test packages between the liquid segments of the at least one of the liquid test packages. According to yet a further aspect of the present invention, the apparatus includes a bubble detector positioned along the fluid conduit at a location in front of the magnet for detecting interfaces between the liquid segments and the air segments of the liquid test packages.

According to a still further aspect of the present invention, a method of analyzing a plurality of samples according to an analysis protocol is provided, wherein each of the samples is contained within a liquid test package comprising a plurality of liquid and air segments including a reagent segment, and wherein during at least a portion of the protocol the reagent segment emits photons. At least one of the liquid test packages includes a buffer segment separated from the reagent segment by an air segment. The method comprises the steps of inserting the liquid test packages into a fluid conduit, flowing the liquid test packages past a first luminometer positioned along the fluid conduit and detecting photons emitted by the reagent segment of the at least one of the liquid test packages, mixing the reagent segment and the buffer segment of the at no least one of the liquid test packages after the photons have been detected, and flowing the liquid test packages past a second luminometer positioned along the fluid conduit and detecting photons emitted by the reagent segments of the liquid test packages other than the at least one of the liquid test packages.

BRIEF DESCRIPTION OF THE DRAWINGS

Further features and advantages of the invention will be apparent upon consideration of the following detailed description of the present invention, taken in conjunction with the following drawings, in which like reference characters refer to like parts, and in which.

DETAILED DESCRIPTION

Figure 3:
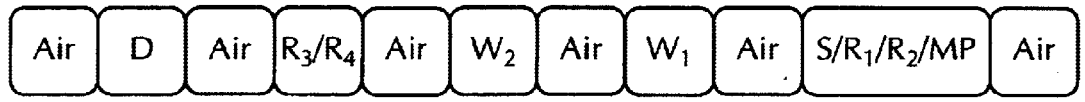
FIG. 3 is a diagram of a prior art test liquid package suitable for conducting a stat immunoassay analysis.
Figure 4:
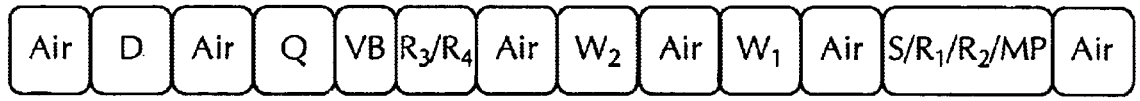
FIG. 4 is a diagram of a liquid test package according to an aspect of the present invention suitable for conducting a stat immunoassay analysis.

Referring to FIG. 4, a liquid test package suitable for conducting a stat immunoassay according to an aspect of the present invention is shown. As shown in FIG. 4, the stat immunoassay liquid test package includes six liquid segments: a mixture of a magnetic particle suspension, sample and first and second reagents designated as S/R$_1$/R$_2$/MP, a first wash designated as W$_1$, a second wash designated as W$_2$, a combination of a third reagent and a fourth reagent designated as R$_3$/R$_4$, a quencher designated as Q, and a marker dye designated a D. The quencher segment Q comprises a buffer having a low pH, such as 1 Molar Tris at pH 7.0. As can be seen in FIG. 4, the quencher segment Q and the third and fourth reagent segment R$_3$/R$_4$ are separated by a particular type of air segment called a vanish bubble, designated as VB. The significance of the vanish bubble VB will be described in more detail below. As shown in FIG. 4, all other liquid segments are separated by an air segment such as those described in connection with the prior art shown in FIGS. 2 and 3.

Figure 5:
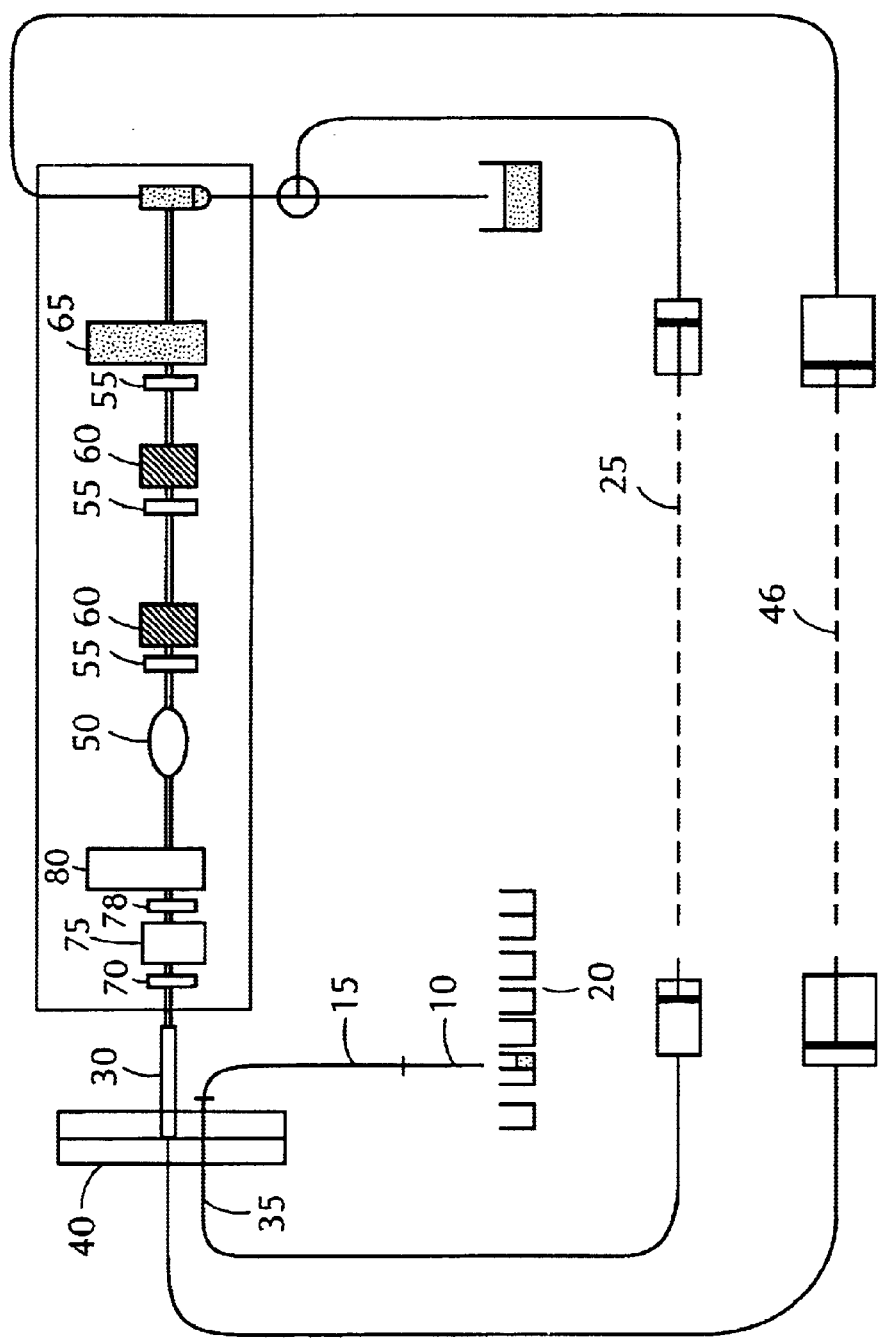
FIG. 5 is a diagram of a capsule chemistry sample liquid analysis system according to an aspect of the present invention configured for conducting a stat immunoassay analysis using the liquid test package shown in FIG. 4.

Referring to FIG. 5, a diagram of a capsule chemistry sample liquid analysis system according to an aspect of the present invention configured for conducting a stat immunoassay analysis using the liquid test package shown in FIG. 4 is shown. As can be seen in FIG. 5, the system includes bubble detector 70, magnet 75, bubble detector 78 and luminometer 80 positioned along analytical line 30 in front of vanish zone 50, bubble detectors 55, magnets 60 and luminometer 65 described above. Preferably, magnet 75 is placed along the analytical line 30 at a distance which is in the range of 4.5 to 7.0 minutes from the shear valve 40, that is, at a distance to which it will take 4.5 to 7.0 minutes for liquid segments to travel from the shear valve 40 in the manner described above and in particular in the '147 and '497 patents and application Ser. No. 09/111,162. Moreover, the vanish zone 50 is preferably placed along the analytical line 30 at a distance which is approximately 10 minutes from the shear valve 40.

Figure 1:
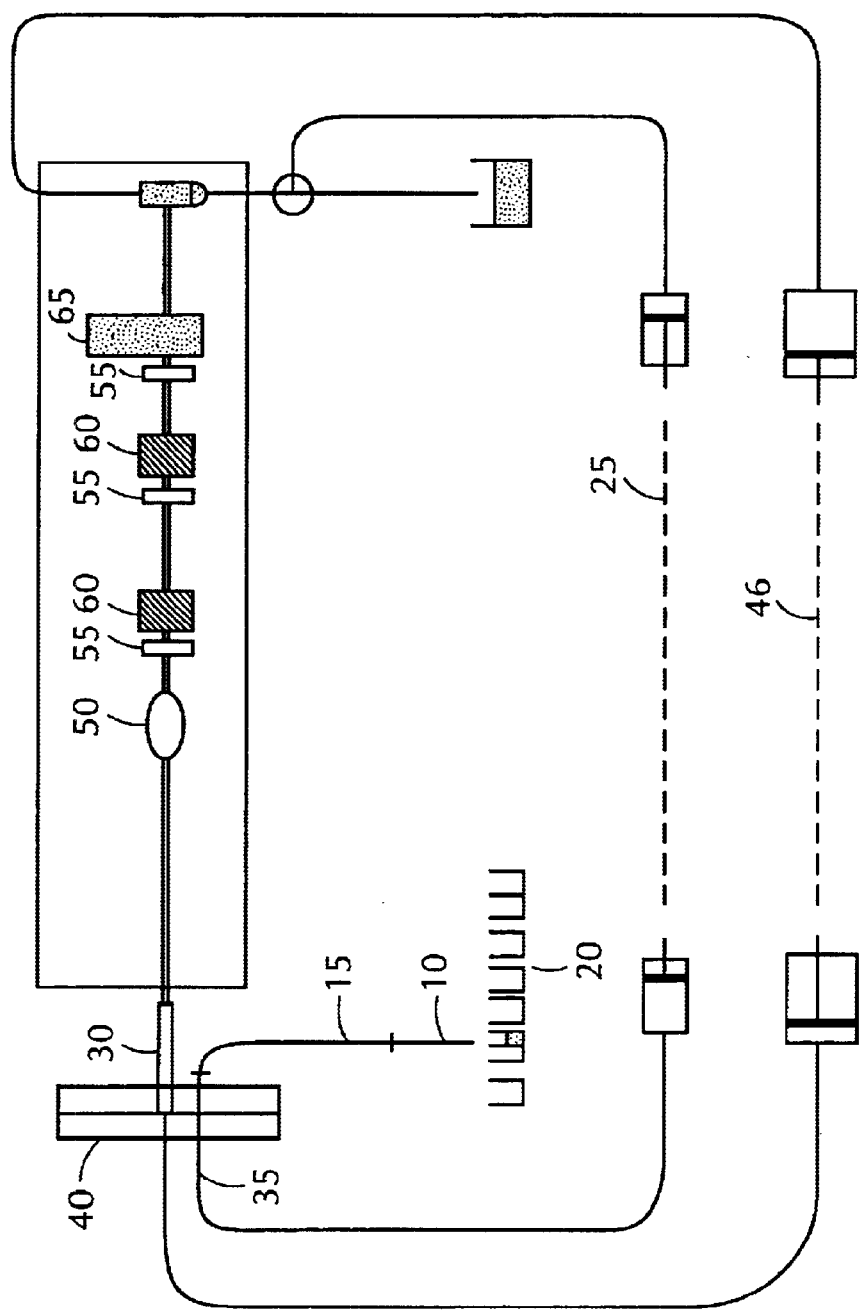
FIG. 1 is a diagram of a prior art capsule chemistry sample liquid analysis system configured for conducting an immunoassay analysis.
Figure 2:
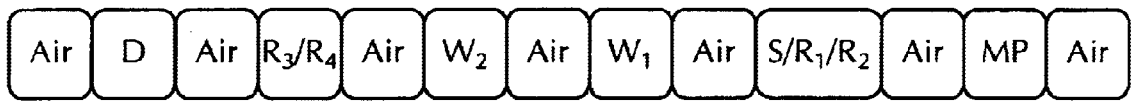
FIG. 2 is a diagram of a prior art liquid test package suitable for conducting a magnetic particle-based heterogeneous immunoassay analysis.

Thus, when immunoassay results for a sample are desired in a relatively short time, i.e., shorter than can be obtained using the liquid test package shown in FIG. 2, a liquid test package shown in FIG. 4 can be created and inserted into analytical line 30. As discussed above, because the magnetic particle suspension is aspirated along with the sample S, the first reagent R$_1$, and the second reagent R$_2$ during the creation of the liquid test package shown in FIG. 4, the immunochemical reactions begin immediately, and in particular the capture of the sandwich on the magnetic particles begins immediately. The magnetic particles in the magnetic particle suspension MP are allowed to react with the sample S and the first and second reagents, R$_1$ and R$_2$, for a predetermined period of time, defined by the assay protocol, and are thereafter separated from the sample S and the first and second reagents R$_1$ and R$_2$ by the magnet 75. In a preferred embodiment of the present invention, the magnetic particles are separated from the sample S and the first and second reagents R$_1$ and R$_2$ 4.5 to 7.0 minutes after being inserted into the analytical line 30. Thereafter, the magnetic particles are transferred by magnet 75 into wash segments W$_1$ and W$_2$, and ultimately into the segment consisting of the third and fourth reagents R$_3$/R$_4$. As noted above, the reaction between the third and fourth reagents and the magnetic particles results in the emission of photons which are in proportion to the analyte concentration in the sample S, i.e., a glowing segment is produced. The emitted photons are detected and measured by the luminometer 80 shown in FIG. 5. Bubble detector 70 is used to sense the interfaces between the liquid and air segments of the liquid test package shown in FIG. 4 so that the transfers described above can be made at the appropriate time. Similarly, bubble detector 78 is used to sense the interfaces between the liquid and air segments so that the emitted photons can be measured at the appropriate time.

As noted above, if the glowing segment were permitted to remain in the analytical line 30 along with the additional glowing segments produced by the conventional immunoassay test packages shown in FIG. 2, it is likely that optical carryover from the stat immunoassay glowing segment would adversely effect the measurements made by the luminometer 65 on the glowing segments produced from the conventional immunoassay test packages. Thus, in order to correct this problem, the system shown in FIG. 5 includes vanish zone 50. As described in detail in the '147 and '497 patents, the vanish zone 50 comprises an enlarged portion of the analytical line 30 which operates in conjunction with a vanish bubble VB to cause a mixing of the liquid segments on either side of the vanish bubble when those liquid segments and vanish bubble enter the vanish zone 50. Thus, when the stat immunoassay glowing segment, i.e., the R$_3$/R$_4$ segment containing the magnet particles, and the quencher segment Q separated by the vanish bubble VB, as shown in FIG. 4, enter the vanish zone 50 at a time after the luminometer 80 has taken appropriate readings, the glowing segment and the quencher Q are mixed with one another. The luminescence reactions that cause the glowing segment to emit photons require a high pH level. When the glowing segment mixes with the low pH buffer, the unstable reaction intermediate that causes the photons to be emitted is stabilized by the lower pH, which reduces the light/photon emission by a measured 99.99%. Thus, when the glowing segment mixes with the low pH buffer comprising the quencher Q, the luminescence reactions, i.e., the light/photon producing reactions, substantially cease and the glowing segments effectively stop emitting photons, thereby eliminating the danger of optical carryover that may effect measurements being made by the luminometer 65. As a result, both short duration, i.e., stat immunoassay, and long duration, i.e., conventional immunoassay, analytical methods can be performed in the same analytical line 30 without one having an adverse effect on the other.

One skilled in the art will appreciate that the present invention can be practiced by other than the described embodiments, which are presented for purposes of illustration and not of limitation.

I claim:

1. A method of analyzing a plurality of samples, said plurality of samples comprising at least a first type and second type of sample, wherein the first and second type of samples include a plurality of segments with at least one of said segments comprising a reagent that emits photons when mixed with another of said segments and wherein said second type of sample includes at least one additional segment, the method comprising:

mixing the at least one reagent segment of the first type of sample with another segment thereof so as to cause the reagent to emit photons;

flowing said first type of sample past a first luminometer positioned along said fluid conduit where data from said first type of sample is collected and analyzed;

halting the emission of light by the reagent of the sample of the first type by mixing said reagent with another segment thereof;

mixing the at least one reagent segment of said second type of sample with another segment thereof so as to cause the reagent to emit photons; and flowing said second type of sample past a second luminometer positioned along said fluid conduit, after the emission of photons by the reagent of the first type of sample has been halted, wherein data from the second type of sample is collected and analyzed.

2. A method according to claim 1, wherein said mixed reagent segment emits said photons as a result of a light producing reaction requiring a high pH level and wherein said halting step further comprises mixing said reagent of the first type of sample with a segment that has a low pH level.

3. A method according to claim 1, wherein the first type of sample is divided into a first segment having a plurality of components, a second segment containing the reagent that emits photons and a third segment containing a quenching component each of said first, second, and third segments being separated by an air segment, the method wherein said mixing of the first sample type comprises transferring a mixing the components of the first segment into the second segment whereby emission of photons commences.

4. A method according to claim 3, wherein said halting step comprises transferring and mixing the components of the first and second segments into the third segment whereby the emission of photons is halted by the quenching component.

* * * * *